(12) United States Patent
Kalnes et al.

(10) Patent No.: US 8,603,399 B2
(45) Date of Patent: Dec. 10, 2013

(54) INTEGRATED OXYGENATE CONVERSION AND PRODUCT CRACKING

(75) Inventors: Tom N. Kalnes, LaGrange, IL (US); Robert B. James, Jr., Northbrook, IL (US); Daniel H. Wei, Naperville, IL (US); Bryan K. Glover, Algonquin, IL (US)

(73) Assignee: UOP LLC, Des Plaines, IL (US)

(*) Notice: Subject to any disclaimer, the term of this patent is extended or adjusted under 35 U.S.C. 154(b) by 1105 days.

(21) Appl. No.: 12/571,841

(22) Filed: Oct. 1, 2009

(65) Prior Publication Data

US 2010/0021357 A1    Jan. 28, 2010

Related U.S. Application Data

(62) Division of application No. 11/293,934, filed on Dec. 5, 2005, now Pat. No. 7,687,671.

(51) Int. Cl.
*B01J 8/18* (2006.01)

(52) U.S. Cl.
USPC ............................ 422/139; 422/648; 585/324

(58) Field of Classification Search
USPC .................. 422/139, 608, 648; 585/640, 324
See application file for complete search history.

(56) References Cited

U.S. PATENT DOCUMENTS

| | | | |
|---|---|---|---|
| 5,744,680 A * | 4/1998 | Mulvaney et al. | 585/640 |
| 6,441,261 B1 * | 8/2002 | Kuechler et al. | 585/639 |
| 6,872,867 B1 * | 3/2005 | Senetar | 585/640 |
| 7,491,315 B2 * | 2/2009 | Eng et al. | 208/113 |
| 2005/0038304 A1 * | 2/2005 | Van Egmond et al. | 585/324 |

* cited by examiner

*Primary Examiner* — Nina Bhat
(74) *Attorney, Agent, or Firm* — Arthur E. Gooding

(57) ABSTRACT

An improved processing system of an oxygenate-containing feedstock for increased production or yield of light olefins. Such processing involves oxygenate conversion to olefins and subsequent cracking of heavier olefins wherein at least a portion of the products from each of the reactors is elevated in pressure, using a common compressor, prior to being routed to a common product fractionation and recovery section. The system further comprises acid gas removal means to remove acid gases from the cracked product gas and that the olefin cracking reactor is a moving bed reactor.

7 Claims, 3 Drawing Sheets

INTEGRATED OXYGENATE CONVERSION AND PRODUCT CRACKING

CROSS-REFERENCE TO RELATED APPLICATION

This application is a Division of prior application Ser. No. 11/293,934 which was filed Dec. 5, 2005 now U.S. Pat. No. 7,687,671, the contents of which are incorporated herein by reference thereto.

BACKGROUND OF THE INVENTION

This invention relates generally to the conversion of oxygenates to olefins and, more particularly, to light olefins.

Light olefins serve as feed materials for the production of numerous chemicals. Light olefins have traditionally been produced through the processes of steam or catalytic cracking. The limited availability and high cost of petroleum sources, however, has resulted in a significant increase in the cost of producing light olefins from such petroleum sources.

The search for alternative materials for light olefin production has led to the use of oxygenates such as alcohols and, more particularly, to the use of methanol, ethanol, and higher alcohols or their derivatives. Molecular sieves such as microporous crystalline zeolite and non-zeolitic catalysts, particularly silicoaluminophosphates (SAPO), are known to promote the conversion of oxygenates to hydrocarbon mixtures, particularly hydrocarbon mixtures composed largely of light olefins.

The amounts of light olefins resulting from such processing can be further increased by reacting, i.e., cracking, heavier hydrocarbon products, particularly heavier olefins such as $C_4$ and $C_5$ olefins, to light olefins. For example, commonly assigned, U.S. Pat. No. 5,914,433 to Marker, the entire disclosure of which is incorporated herein by reference, discloses a process for the production of light olefins comprising olefins having from 2 to 4 carbon atoms per molecule from an oxygenate feedstock. The process comprises passing the oxygenate feedstock to an oxygenate conversion zone containing a metal aluminophosphate catalyst to produce a light olefin stream. A propylene and/or mixed butylene stream is fractionated from said light olefin stream and cracked to enhance the yield of ethylene and propylene products. This combination of light olefin product and propylene and butylene cracking in a riser cracking zone or a separate cracking zone provides flexibility to the process which overcomes the equilibrium limitations of the aluminophosphate catalyst. In addition, the invention provides the advantage of extended catalyst life and greater catalyst stability in the oxygenate conversion zone.

Mechanical devices are used for driving fluids to appropriate locations at desired pressures. A pump is a mechanical device or machine that is used to force a liquid phase material from one pressure to a higher pressure. The mechanical work performed by a pump is proportional to the volume of the liquid being pumped times the differential pressure which is outlet pressure minus inlet pressure. Some of the mechanical work is expended in transferring the liquid from one location to another. Pumps are not typically sufficiently powerful to change the volume of the liquid being pumped. A compressor is a mechanical device or machine that is used to force a vapor phase material from one pressure to a higher pressure. The mechanical work performed by a compressor is proportional to the volume of the vapor being pumped times the differential pressure. Compressors typically decrease the volume of the vapor being pumped. Material in the liquid phase is always much more dense than material in the vapor phase. For the same mass of material, the work required to pump liquid is always much less than the work required to pump vapor via compressor.

Further improvements such as relating to reducing or minimizing system processing costs and complexity, however, are desired and are being sought.

In view thereof, there is a need and a demand for improved processing and systems for the conversion of oxygenates to olefins and, more particularly, for such processing and systems such as to result in an increase in the relative amount of light olefins.

SUMMARY OF THE INVENTION

A general object of the invention is to provide or result in improved processing of an oxygenate-containing feedstock to light olefins.

A more specific objective of the invention is to overcome one or more of the problems described above.

The general object of the invention can be attained, at least in part, through a process for producing light olefins from an oxygenate-containing feedstock. In accordance with one preferred embodiment, such a process involves contacting the oxygenate-containing feedstock in an oxygenate conversion reactor with an oxygenate conversion catalyst and at reaction conditions effective to convert the oxygenate-containing feedstock to an oxygenate conversion product stream comprising fuel gas hydrocarbons, light olefins, and $C_{4+}$ hydrocarbons. At least a portion of the oxygenate conversion product stream is subsequently compressed via a first compressor. The compressed oxygenate conversion product stream is treated in a gas concentration system to recover light olefins and to form a $C_{4+}$ hydrocarbon stream. At least a portion of the $C_{4+}$ hydrocarbon stream is contacted in an olefin cracking reactor with an olefin cracking catalyst and at reaction conditions effective to convert $C_4$ and $C_5$ olefins therein contained to a cracked olefins effluent stream comprising light olefins. At least a portion of the cracked olefins effluent stream is returned to the first compressor for combination with the oxygenate conversion product stream and subsequent treatment in the gas concentration system.

The prior art generally fails to provide processing of oxygenates to olefins, particularly such as to result in an increase in the relative amount of light olefins, and which processing is one or more as simple, effective, as economic as may be desired.

In another embodiment, there is provided a process for producing light olefins from a methanol-containing feedstock. The process involves contacting the methanol-containing feedstock in a methanol conversion reactor fluidized reaction zone with a methanol conversion catalyst and at reaction conditions effective to convert the methanol-containing feedstock to a methanol conversion product stream comprising fuel gas hydrocarbons, light olefins, and $C_{4+}$ hydrocarbons. At least a portion of the methanol conversion product stream is subsequently compressed via a first compressor. The compressed methanol conversion product stream it treated in a gas concentration system to recover light olefins and to form a fuel gas hydrocarbon stream and a $C_{4+}$ hydrocarbon stream. The $C_{4+}$ hydrocarbon stream is fractionated to form a process stream comprising $C_{4+}$ through $C_{6-}$ hydrocarbons and a purge stream comprising $C_{7+}$ hydrocarbons. The process stream is contacted in an olefin cracking reactor with an olefin cracking catalyst and at reaction conditions effective to convert $C_4$ and $C_5$ olefins therein contained to a cracked olefins effluent stream comprising light olefins. The cracked olefins effluent stream is separated into a first stream comprising $C_1$ and $C_2$ hydrocarbons and a second stream comprising a remainder of the olefin cracking product stream. The first stream is returned to the first compressor for combination with the oxygenate conversion product stream and subsequent treatment in the gas concentration system and the second stream is introduced to the gas concentration system without compression.

There is also provided a system for converting oxygenates to light olefins. In accordance with one embodiment, a reactor is provided for contacting an oxygenate-containing feedstream with catalyst and converting the oxygenate-containing feedstream to an oxygenate conversion product stream comprising fuel gas hydrocarbons, light olefins, and $C_{4+}$ hydrocarbons. A first compressor is provided to compress at least a portion of the oxygenate conversion product stream to form a compressed oxygenate conversion product stream. A gas concentration system is provided to treat the compressed oxygenate conversion product stream to recover light olefins and to form a $C_{4+}$ hydrocarbon stream. The system further includes a reactor for contacting at least a portion of the $C_{4+}$ hydrocarbon stream with catalyst and converting $C_4$ and $C_5$ olefins therein contained to a cracked olefin effluent stream comprising light olefins. A first return line is provided wherein at least a portion of the cracked olefin effluent stream is introduced into the first compressor and subsequently processed through the gas concentration system.

As used herein, references to "light olefins" are to be understood to generally refer to $C_2$ and $C_3$ olefins, i.e., ethylene and propylene.

Other objects and advantages will be apparent to those skilled in the art from the following detailed description taken in conjunction with the appended claims and drawings.

DETAILED DESCRIPTION OF THE INVENTION

Oxygenate-containing feedstock can be converted to light olefins in a catalytic reaction and heavier hydrocarbons (e.g., $C_{4+}$ hydrocarbons) formed during such processing can be subsequently cracked to increase the light olefins (e.g., $C_2$ and $C_3$ olefins) produced or resulting therefrom. In accordance with a preferred embodiment, at least a portion of the oxygenate conversion product stream and at least a portion of the olefin cracking product stream are elevated in pressure, together or separately, through the same compressor prior to being routed through an appropriate gas concentration system.

Figure 1:
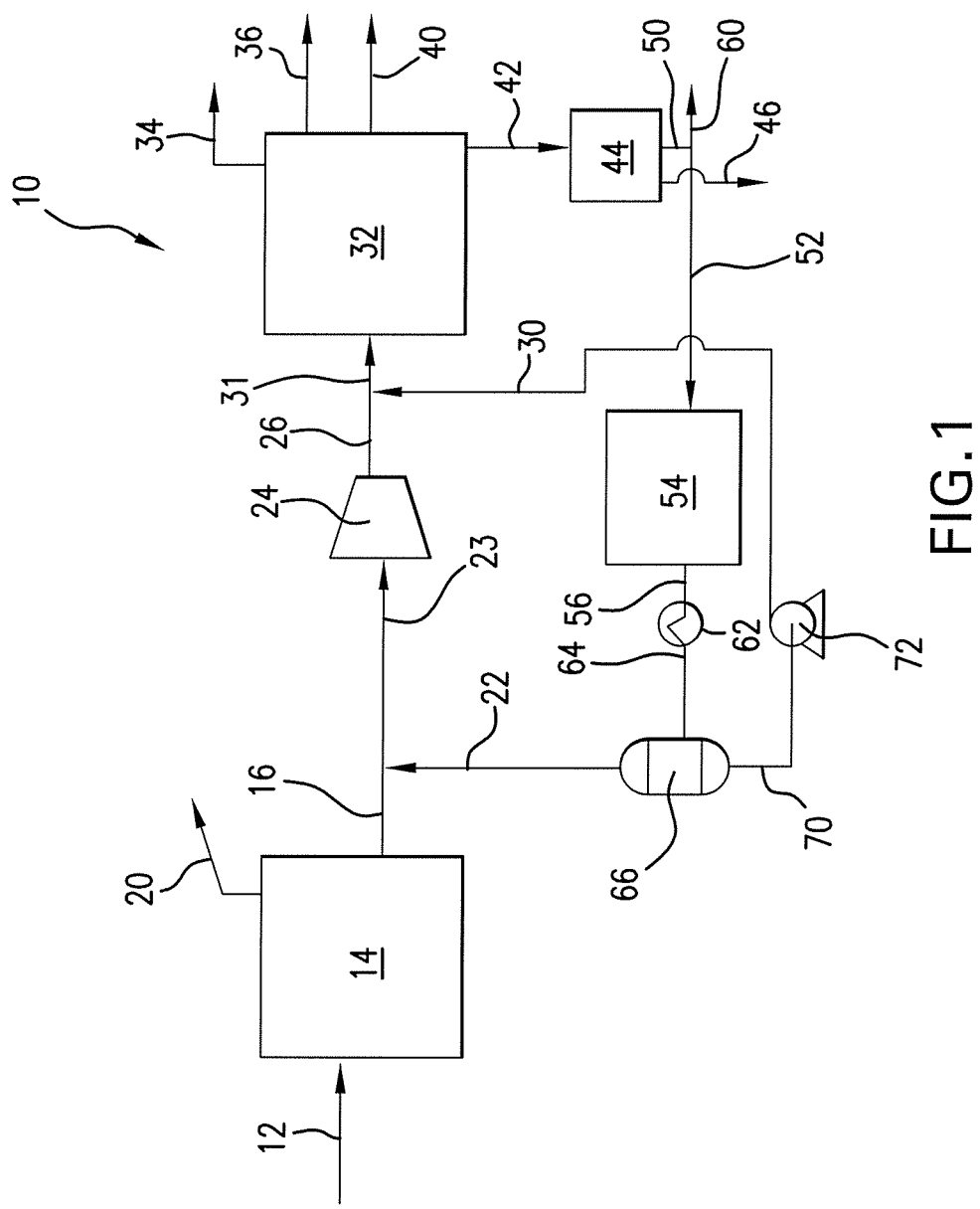
FIG. 1 is a simplified schematic diagram of a process for the conversion of an oxygenate-containing feedstock to olefins in accordance with one embodiment.

FIG. 1 schematically illustrates a system, generally designated by the reference numeral 10, for the conversion of an oxygenate-containing feedstock to olefins in accordance with one embodiment.

More particularly, an oxygenate-containing feedstock 12 such as generally composed of light oxygenates such as one or more of methanol, ethanol, dimethyl ether, diethyl ether, or mixtures thereof, is introduced into an oxygenate conversion reactor section 14 wherein the oxygenate-containing feedstock contacts with an oxygenate conversion catalyst at reaction conditions effective to convert the oxygenate-containing feedstock to an oxygenate conversion product stream comprising fuel gas hydrocarbons, light olefins, and $C_{4+}$ hydrocarbons, in a manner as is known in the art, such as, for example, utilizing a fluidized bed reactor.

As will be appreciated by those skilled in the art and guided by the teachings herein provided, such a feedstock may be commercial grade methanol, crude methanol or any combination thereof. Crude methanol may be an unrefined product from a methanol synthesis unit. Those skilled in that art and guided by the teachings herein provided will understand and appreciate that in the interest of factors such as improved catalyst stability, embodiments utilizing higher purity methanol feeds may be preferred. Thus, suitable feeds may comprise methanol or a methanol and water blend, with possible such feeds having a methanol content of between about 65% and about 100% by weight, preferably a methanol content of between about 80% and about 100% by weight and, in accordance one preferred embodiment, a methanol content of between about 95% and about 100% by weight A methanol-to-olefin unit designed to process about 2,500,000 metric tons per year of 95 wt. % methanol may have a feed rate of preferably between about 1500 and about 4000 kMTA and more preferably between about 2000 and about 3500 kMTA. The feedstream may comprise between about 0 and about 35 wt. % and more preferably between about 5 and about 30 wt. % water. The methanol in the feed stream may comprise between about 70 and about 100 wt. % and more preferably between about 75 and about 95 wt. % of the feedstream. The ethanol in the feedstream may comprise between about 0.01 and about 0.5 wt. % and more typically between about 0.1 and about 0.2 wt. % of the feedstream although higher concentrations may be beneficial. When methanol is the primary component in the feedstream, the higher alcohols in the feedstream may comprise between about 200 and about 2000 wppm and more typically between about 500 and about 1500 wppm. Additionally, when methanol is the primary component in the feedstream, dimethyl ether in the feedstream may comprise between about 100 and about 20,000 wppm and more typically between about 200 and about 10,000 wppm.

Reaction conditions for the conversion of oxygenates to light olefins are known to those skilled in the art. Preferably, in accordance with particular embodiments, reaction conditions comprise a temperature between about 200° and about 700° C., more preferably between about 300° and 600° C., and most preferably between about 400° and about 550° C. As will be appreciated by those skilled in the art and guided by the teachings herein provided, the reactions conditions are generally variable such as dependent on the desired products. For example, if increased ethylene production is desired, then operation at a reactor temperature between about 475° and about 550° C. and more preferably between about 500° and about 520° C., may be preferred. If increased propylene production is desired, then operation at a reactor temperature between about 350° and about 475° C. and more preferably between about 400° and about 430° C. may be preferred. The light olefins produced can have a ratio of ethylene to propylene of between about 0.5 and about 2.0 and preferably between about 0.75 and about 1.25. If a higher ratio of ethylene to propylene is desired, then the reaction temperature is higher than if a lower ratio of ethylene to propylene is desired. The preferred feed temperature range is between about 120° and about 210° C. More preferably the feed temperature range is between about 180° and 210° C. In accordance with one preferred embodiment, the temperature is desirably maintained below 210° C. to avoid or minimize thermal decomposition.

The oxygenate conversion reactor section 14 produces or results in an oxygenate conversion product or effluent stream 16 generally comprising fuel gas hydrocarbons, light olefins, and $C_{4+}$ hydrocarbons. The oxygenate conversion reactor section 14 may also, as shown, produce or result in a wastewater stream 20, such as, for example, may contain low levels of unreacted alcohols as well as small amounts of oxygenated byproducts such as low molecular weight aldehydes and organic acids, and such as may be appropriately treated and disposed or recycled.

The oxygenate conversion product stream 16 and a recycle stream 22, such as described in greater detail below, and such as together form a process stream designated by the reference numeral 23, are appropriately processed through a compressor 24. The resulting compressed oxygenate conversion product stream 26 and, if desired, a recycle stream 30, described in greater detail below, and such as together form a process stream designated by the reference numeral 31, are introduced into an appropriate gas concentration system 32.

Gas concentration systems such as used for the processing of the products resulting from such oxygenate conversion processing are well known to those skilled in the art and do not generally form limitations on the broader practice of the invention as those skilled in the art and guided by the teachings herein provided will appreciate.

In the gas concentration system 32, the process stream 31 such as constituting the compressed oxygenate conversion product stream 26 and, if used, the recycle stream 30, is processed to provide a fuel gas stream 34, an ethylene stream 36, a propylene stream 40 and a mixed $C_{4+}$ hydrocarbon stream 42, such as generally composed of butylene and heavier hydrocarbons.

The mixed $C_{4+}$ hydrocarbon stream 42 is subjected to a fractionation section 44 such as to form a purge stream 46 such as generally comprising $C_{7+}$ hydrocarbons and a process stream 50 such as generally comprising $C_4$, $C_5$ and $C_6$ hydrocarbons. At least a portion of the process stream 50, e.g., the process stream portion 52, is introduced into an olefin cracking reactor section 54, such as in the form of a fixed bed reactor, as is known in the art and wherein the process stream portion 52 contacts with an olefin cracking catalyst and at reaction conditions, in a manner as is known in the art, effective to convert $C_4$ and $C_5$ olefins therein contained to a cracked olefins effluent stream 56 comprising light olefins.

A purge stream 60 is shown whereby $C_4$-$C_6$ paraffin compounds and the like may desirably be purged from the material stream being processed in the system 10, in a manner such as known in the art. As will be appreciated by those skilled in the art and guided by the teachings herein provided, such compounds generally do not convert very well in olefin cracking reactors. Consequently, such purging can avoid the undesirable build-up of such compounds within the process system 10.

The cracked olefins effluent stream 56 is processed through a cooler 62 to form a process stream 64. The process stream 64 is then processed through a gas-liquid separator 66 to form a recycle stream of gaseous material, such as constituting the above-identified recycle stream 22 and such as generally comprising $C_1$ and $C_2$ hydrocarbons. As shown, the recycle stream 22 can be combined with the oxygenate conversion product stream 16 and returned to the compressor 24. The gas-liquid separator 66 also forms a process stream 70 such as constituting the remainder of the cracked olefins effluent such as generally comprising liquid material and such as may be conveyed via a pump 72 such as to constitute the recycle stream 30, identified above, and such as for combination with the compressed oxygenate conversion product stream 26 and subsequent processing through the gas concentration system 32. In accordance with the illustrated embodiment, the recycle stream 30 can desirably be introduced to the gas concentration system 32 without first undergoing compression.

The system 10 desirably serves to increase or maximize the conversion of the oxygenate feedstock to light olefins while reducing or minimizing the production of $C_{4+}$ liquid. Further such an embodiment desirably reduces or minimizes capital costs by utilizing a single or common compressor for the treatment of the effluent from the two reactor sections, i.e., the oxygenate conversion reactor and the olefin cracking reactor. Such embodiment still further reduces or minimizes capital costs by utilizing a single or common gas concentration system, such as composed of appropriate product fractionation and recovery sections, for the treatment of the effluent from the two reactor sections.

Figure 2:
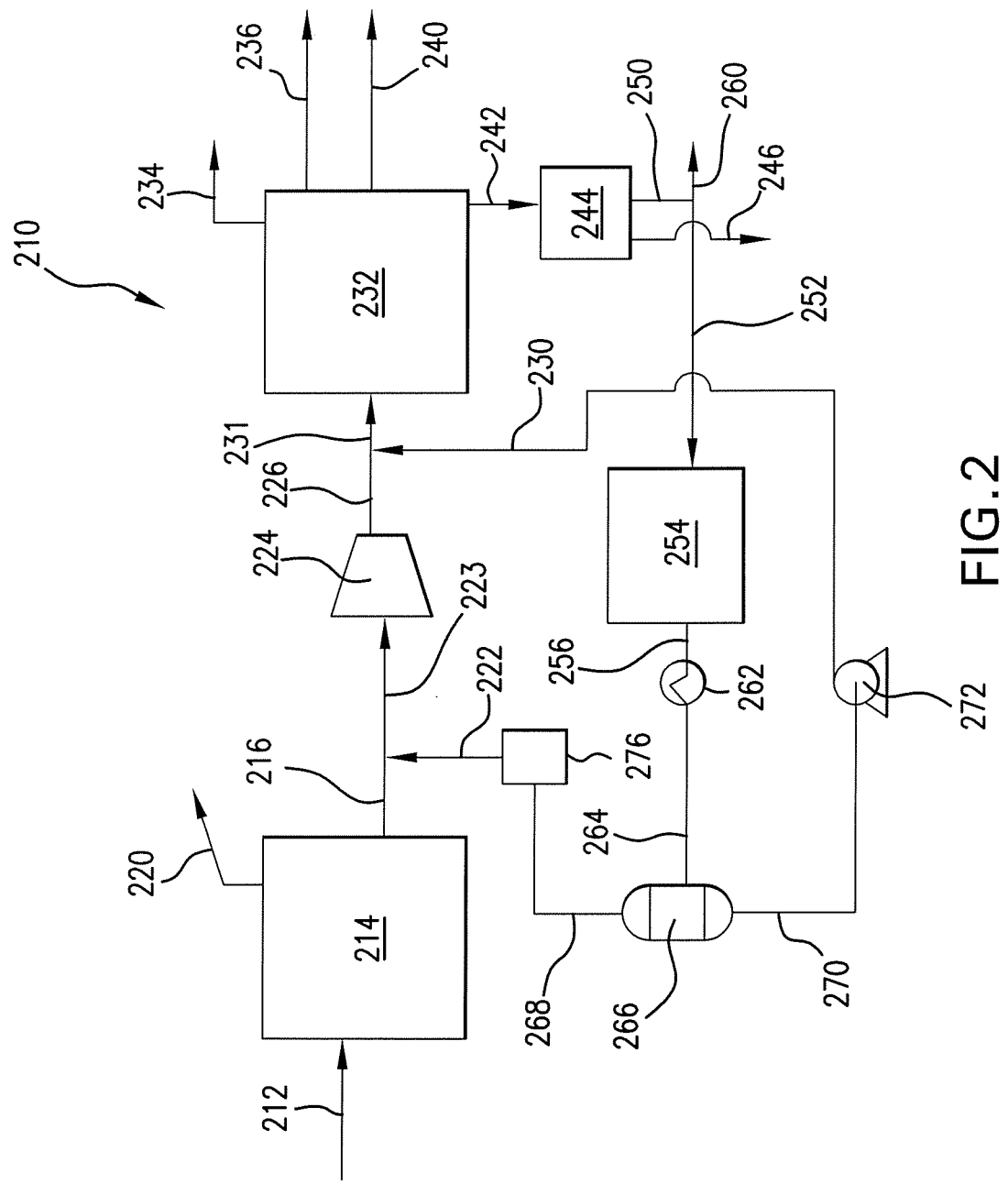
FIG. 2 is a simplified schematic diagram of a process for the conversion of an oxygenate-containing feedstock to olefins in accordance with another embodiment.

FIG. 2 illustrates a system, generally designated by the reference numeral 210, for the conversion of an oxygenate-containing feedstock to olefins in accordance with another embodiment. The system 210 is generally similar to the system 10 shown in FIG. 1 and described above.

More particularly, an oxygenate-containing feedstock 212 is introduced into an oxygenate conversion reactor section 214 wherein the oxygenate-containing feedstock contacts with an oxygenate conversion catalyst and at reaction conditions effective to convert the oxygenate-containing feedstock to an oxygenate conversion product stream comprising fuel gas hydrocarbons, light olefins, and $C_{4+}$ hydrocarbons, in a manner as is known in the art.

The oxygenate conversion reactor section 214 produces or results in an oxygenate conversion product stream 216 generally comprising fuel gas hydrocarbons, light olefins, and $C_{4+}$ hydrocarbons. The oxygenate conversion reactor section 214 may also, as shown, produce or result in wastewater stream 220, such as may be appropriately treated and disposed or recycled.

The oxygenate conversion product stream 216 and a recycle stream 222, such as described in greater detail below, and such as together form a process stream designated by the reference numeral 223, are appropriately processed through a compressor 224. The resulting compressed oxygenate conversion product stream 226 and, if desired, a recycle stream 230, described in greater detail below, and such as together form a process stream designated by the reference numeral 231, are introduced into an appropriate gas concentration system 232.

In the gas concentration system 232, the process stream 231 such as constituting the compressed oxygenate conversion product stream 226 and, if used, the recycle stream 230, is processed to provide a fuel gas stream 234, an ethylene stream 236, a propylene stream 240 and a mixed $C_{4+}$ hydrocarbon stream 242, such as generally composed of butylene and heavier hydrocarbons.

The mixed $C_{4+}$ hydrocarbon stream 242 is subjected to a fractionation section 244 such as to form a purge stream 246 such as generally comprising $C_{7+}$ hydrocarbons and a process stream 250 such as generally comprising $C_4$, $C_5$ and $C_6$ hydrocarbons. At least a portion of the process stream 250, e.g., the process stream portion 252, is introduced into an olefin cracking reactor section 254, such as in the form of a fixed bed reactor, as is known in the art and wherein the process stream portion 252 contacts with an olefin cracking catalyst and at reaction conditions, in a manner as is known in the art, effective to convert $C_4$ and $C_5$ olefins therein contained to a cracked olefins effluent stream 256 comprising light olefins.

Similar to the system 10 described above, a purge stream 260 is shown whereby $C_4$-$C_6$ paraffin compounds and the like may desirably be purged from the material stream being processed in the system 210, such as in a manner known in the art.

The cracked olefins effluent stream 256 is processed through a cooler 262 to form a process stream 264. The process stream 264 is then processed through a gas-liquid separator 266 to form a stream 268 of gaseous material and a stream 270 such as constituting the remainder of the cracked olefins effluent such as generally comprising liquid material and such as may be conveyed via a pump 272 such as to constitute the recycle stream 230, identified above. As shown, the recycle stream 230 can desirably be introduced to the gas concentration system 232 without first undergoing compression.

The system 210 primarily differs from the system 10, described above, by the inclusion of an acid gas separation section 276. The acid gas separation section 276 treats the stream 268 of gaseous material to remove acid gas therefrom such as may normally be present therein in relatively minor or trace amounts. With such acid gas removal, a recycle stream of gaseous material is formed, such as constituting the above-identified recycle stream 222 and such as generally comprising $C_1$ and $C_2$ hydrocarbons. Such acid gas removal can be realized by various manners known in the art and can desirably occur prior to return of the material to the compressor 224. Such acid gas removal can significantly facilitate downstream material handling and permit the utilization less costly processing hardware. For example, through such acid gas removal, $H_2S$ can desirably be kept out of the various process and product streams and the need for the use of more expensive metallurgy in product compressors and various downstream equipment can be minimized or preferably avoided.

Figure 3:
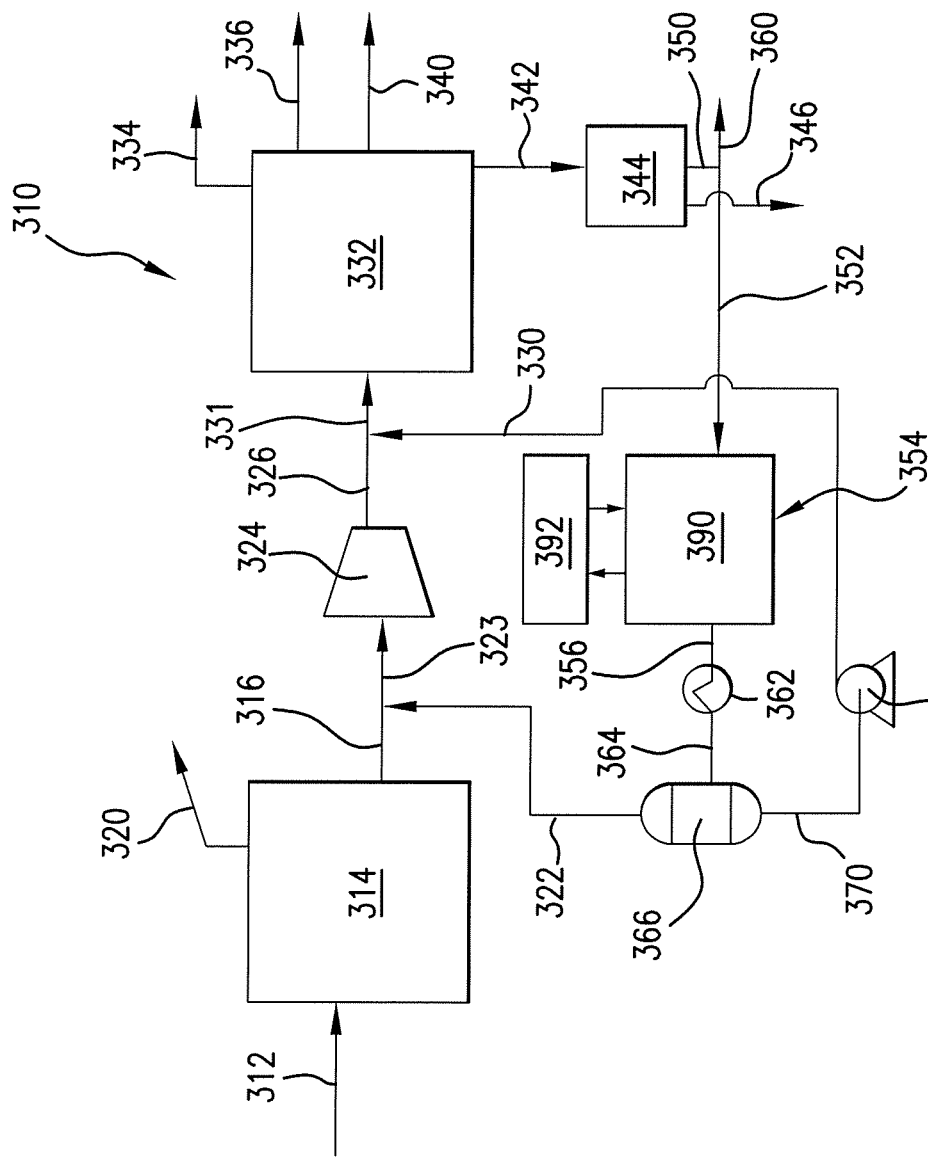
FIG. 3 is a simplified schematic diagram of a process for the conversion of an oxygenate-containing feedstock to olefins in accordance with yet another embodiment.

While embodiments utilizing a fixed bed olefin cracking reactor unit have been described above, those skilled in the art and guided by the teachings herein provided will appreciate that the broader practice of the invention is not necessarily so limited. To that end, reference is now made to FIG. 3 which illustrates a system, generally designated by the reference numeral 310, for the conversion of an oxygenate-containing feedstock to olefins in accordance with yet another embodiment and wherein an olefin cracking reactor unit having the form of a moving bed reactor is utilized. The system 310 is generally similar to the system 10 shown in FIG. 1 and described above.

More particularly, an oxygenate-containing feedstock 312 is introduced into an oxygenate conversion reactor section 314 wherein the oxygenate-containing feedstock contacts with an oxygenate conversion catalyst and at reaction conditions effective to convert the oxygenate-containing feedstock to an oxygenate conversion product stream comprising fuel gas hydrocarbons, light olefins, and $C_{4+}$ hydrocarbons, in a manner as is known in the art.

The oxygenate conversion reactor section 314 produces or results in an oxygenate conversion product stream 316 generally comprising fuel gas hydrocarbons, light olefins, and $C_{4+}$ hydrocarbons. The oxygenate conversion reactor section 314 may also, as shown, produce or result in wastewater stream 320, such as may be appropriately treated and disposed or recycled.

The oxygenate conversion product stream 316 and a recycle stream 322, such as described in greater detail below, and such as together form a process stream designated by the reference numeral 323, are appropriately processed through a compressor 324. The resulting compressed oxygenate conversion product stream 326 and, if desired, a recycle stream 330, described in greater detail below, and such as together form a process stream designated by the reference numeral 331, are introduced into an appropriate gas concentration system 332.

In the gas concentration system 332, the process stream 331 such as constituting the compressed oxygenate conversion product stream 326 and, if used, the recycle stream 330, is processed to provide a fuel gas stream 334, an ethylene stream 336, a propylene stream 340 and a mixed $C_{4+}$ hydrocarbon stream 342, such as generally composed of butylene and heavier hydrocarbons.

The mixed $C_{4+}$ hydrocarbon stream 342 is subjected to a fractionation section 344 such as to form a purge stream 346 such as generally comprising $C_{7+}$ hydrocarbons and a process stream 350 such as generally comprising $C_4$, $C_5$ and $C_6$ hydrocarbons. At least a portion of the process stream 350, e.g., the process stream portion 352, is introduced into an olefin cracking reactor section 354 wherein the process stream portion 352 contacts with an olefin cracking catalyst and at reaction conditions, in a manner as is known in the art, effective to convert $C_4$ and $C_5$ olefins therein contained to a cracked olefins effluent stream 356 comprising light olefins.

Similar to the system 110 described above, a purge stream 360 is shown whereby $C_4$-$C_6$ paraffin compounds and the like may desirably be purged from the material stream being processed in the system 310, such as in a manner known in the art, and such as to avoid the undesirable build-up of such compounds within the process system 310.

The cracked olefins effluent stream 356 is processed through a cooler 362 to form a process stream 364. The process stream 364 is then processed through a gas-liquid separator 366 to form a recycle stream of gaseous material, such as constituting the above-identified recycle stream 322 and such as generally comprising $C_1$ and $C_2$ hydrocarbons. The gas-liquid separator 366 also forms a process stream 370 such as constituting the remainder of the cracked olefins effluent such as generally comprising liquid material and such as may be conveyed via a pump 372 such as to constitute the recycle stream 330, identified above, and such as for combination with the compressed oxygenate conversion product stream 326 and subsequent processing through the gas concentration system 332. As shown, the recycle stream 330 can desirably be introduced to the gas concentration system 332 without first undergoing compression.

The system 310 primarily differs from the system 10, described above, by requiring that the olefin cracking reactor section 354 includes a moving bed reactor 390 which allows at least a portion of the catalyst from the moving bed reactor 390 to be regenerated on a continuous or semi-continuous basis in a separate but integrated regeneration zone 392.

The incorporation and use of moving bed (radial flow) reactor with continuous or semi-continuous catalyst regeneration for the cracking of the heavy recycle olefins can desirably serve to minimize the capital costs for the processing arrangement. For example, utilization of such a moving bed reactor with a continuous catalyst regenerator can desirably allow the associated olefin cracking reactor to operate at a higher average conversion as compared to a typical swing bed reactor system. In addition, the reactor section effluent from such a moving bed reactor desirably provides or results in a steadier composition such as may desirably simplify the design and operation of downstream fractionators.

If desired, the system 310 can be appropriately modified to incorporate an acid gas separation section (not shown), such as identified and described above relative to the system 210, shown in FIG. 2.

While the invention has been described above making specific reference to the processing of an oxygenate-containing feedstock comprising light oxygenates such as one or more of methanol, ethanol, dimethyl ether, diethyl ether, or mixtures thereof, those skilled in the art and guided by the teachings herein provided will appreciate that the broader practice of the invention is not necessarily so limited. More particularly, suitable "oxygenate-containing" feedstocks employed in the practice of the invention are to be understood to include alcohols, ethers and carbonyl compounds (aldehydes, ketones, carboxylic acids and the like). Moreover, such suitable oxygenate-containing feedstocks preferably contain from 1 to about 10 carbon atoms and, more preferably, contains from 1 to about 4 carbon atoms. Suitable reactants include lower straight or branched chain alkanols, their unsaturated counterparts. Representatives of suitable oxygenate compounds include: methanol; dimethyl ether; ethanol; diethyl ether; methyl ethyl ether; formaldehyde; dimethyl ketone; acetic acid; and mixtures thereof.

Embodiments, such as described above, desirably provide or result in improved processing of oxygenates to olefins, particularly such as to result in an increase in the relative amount of light olefins, and which processing is desirably more simple, effective, and/or economic than heretofore reasonably possible. In accordance with particular such embodiments, an oxygenate-containing feedstock can be converted to light olefins in a catalytic reaction and heavier hydrocarbons (e.g., $C_{4+}$ hydrocarbons) formed during such processing can be subsequently cracked to increase the light olefins (e.g., $C_2$ and $C_3$ olefins) produced or resulting therefrom, with at least a portion of the oxygenate conversion product stream and at least a portion of the oxygenate conversion product stream being elevated in pressure, together or separately, through the same compressor prior to being routed through an appropriate gas concentration system.

The invention illustratively disclosed herein suitably may be practiced in the absence of any element, part, step, component, or ingredient which is not specifically disclosed herein.

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

The invention claimed is:

1. A system for converting oxygenates to light olefins, said system comprising:
    a reactor for contacting an oxygenate-containing feedstream with catalyst and converting the oxygenate-containing feedstream to an oxygenate conversion product stream comprising fuel gas hydrocarbons, light olefins, and $C_{4+}$ hydrocarbons;
    a first compressor to compress at least a portion of the oxygenate conversion product stream to form a compressed oxygenate conversion product stream;
    a gas concentration system to treat the compressed oxygenate conversion product stream to recover light olefins and to form a $C_{4+}$ hydrocarbon stream;
    a reactor for contacting at least a portion of the $C_{4+}$ hydrocarbon stream with catalyst and converting $C_4$ and $C_5$ olefins therein contained to a cracked olefin effluent stream comprising light olefins; and
    a first return line wherein at least a portion of the cracked olefin effluent stream is introduced into the first compressor and subsequently processed through the gas concentration system.

2. The system of claim 1 additionally comprising:
    a cracked olefin effluent separation system effective to separate the cracked olefin effluent into a first stream comprising $C_1$ and $C_2$ hydrocarbons and a second stream comprising a remainder of the cracked olefin effluent; and
    a second return line wherein at least a portion of the second stream is introduced into the gas concentration system without prior passage through the first compressor;
wherein the portion of the cracked olefin effluent stream introduced into the first compressor and subsequently processed through the gas concentration system comprises at least a portion of the first stream.

3. The system of claim 2 additionally comprising an acid gas neutralization reactor disposed between the cracked olefin effluent separation system and the first compressor, the acid gas neutralization reactor effective to neutralize acid gas present in the first stream prior to passage to the first compressor.

4. The system of claim 1 wherein the olefin cracking reactor is a fixed bed reactor.

5. The system of claim 1 wherein the olefin cracking reactor is a moving bed reactor.

6. The system of claim 5 additionally comprising a continuous catalyst regenerator wherein the olefin cracking catalyst is continuously regenerated.

7. The system of claim 1 additionally comprising a fractionator to fractionate the $C_{4+}$ hydrocarbon stream to form a process stream comprising $C_{4+}$ through $C_{6-}$ hydrocarbons and wherein the at least a portion of the $C_{4+}$ hydrocarbon stream contacted with the catalyst in the reactor comprises at least a portion of the process stream comprising $C_{4+}$ through $C_{6-}$ hydrocarbons.

* * * * *